US010111458B1

(12) United States Patent
Marshall et al.

(10) Patent No.: US 10,111,458 B1
(45) Date of Patent: Oct. 30, 2018

(54) PROCESS FOR INHIBITING FORMATION OF NITROSAMINES

(71) Applicant: R. J. Reynolds Tobacco Company, Winston-Salem, NC (US)

(72) Inventors: Jerry Wayne Marshall, Stokesdale, NC (US); Jo A. Hart, Winston-Salem, NC (US); Anthony A. Gerardi, Winston-Salem, NC (US); Annett Milling, Winston-Salem, NC (US); Robert Reinbold, Collierville, TN (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 189 days.

(21) Appl. No.: 14/713,564

(22) Filed: May 15, 2015

Related U.S. Application Data

(60) Provisional application No. 61/994,193, filed on May 16, 2014.

(51) Int. Cl.
*A24B 15/20* (2006.01)
*A24B 15/24* (2006.01)
*A01N 63/00* (2006.01)

(52) U.S. Cl.
CPC .............. *A24B 15/20* (2013.01); *A01N 63/00* (2013.01); *A24B 15/245* (2013.01)

(58) Field of Classification Search
CPC ........ A24B 15/20; A24B 15/245; A01N 63/00
See application file for complete search history.

(56) References Cited

U.S. PATENT DOCUMENTS

| | | | |
|---|---|---|---|
| 3,847,164 A | 11/1974 | Mattina et al. | |
| 4,131,117 A | 12/1978 | Kite et al. | |
| 4,253,929 A | 3/1981 | Keritsis | |
| 4,301,817 A | 11/1981 | Keritsis | |
| 4,308,877 A | 1/1982 | Mattina | |
| 4,375,734 A | 3/1983 | Kozloff et al. | |
| 4,524,786 A | 6/1985 | Gaisch et al. | |
| 4,556,073 A | 12/1985 | Gravely et al. | |
| 4,557,280 A | 12/1985 | Gravely et al. | |
| 4,566,469 A | 1/1986 | Semp et al. | |
| 4,572,219 A | 2/1986 | Gaisch et al. | |
| 4,589,428 A | 5/1986 | Keritsis | |
| 4,622,982 A | 11/1986 | Gaisch et al. | |
| 4,651,759 A | 3/1987 | Uydess | |
| 4,685,478 A | 8/1987 | Malik et al. | |
| 4,709,710 A | 12/1987 | Gaisch et al. | |
| 4,828,999 A | 5/1989 | Jackson | |
| 4,851,240 A | 7/1989 | Day et al. | |
| 5,422,108 A | 6/1995 | Mirkov et al. | |
| 5,424,395 A | 6/1995 | Bascomb et al. | |
| 5,810,020 A | 9/1998 | Northway et al. | |
| 6,461,608 B1 | 10/2002 | Averback et al. | |
| 6,564,808 B1 | 5/2003 | Hempfling et al. | |
| 6,805,134 B2 | 10/2004 | Peele | |
| 6,907,887 B2 | 6/2005 | Conkling | |
| 6,911,541 B2 | 6/2005 | Conkling et al. | |
| 7,211,426 B2 | 5/2007 | Bruessow et al. | |
| 7,549,425 B2 | 6/2009 | Koga et al. | |
| 7,549,426 B2 | 6/2009 | Koga et al. | |
| 7,550,283 B2 | 6/2009 | Holland et al. | |
| 7,556,046 B2 | 7/2009 | Koga et al. | |
| 7,650,891 B1 | 1/2010 | Groves et al. | |
| 7,674,467 B2 | 3/2010 | Sulakvelidze et al. | |
| 7,906,131 B2 | 3/2011 | Brower | |
| 7,992,575 B2 | 8/2011 | Cui et al. | |
| 8,151,804 B2 | 4/2012 | Williams | |
| 8,507,650 B2 | 8/2013 | Gabriel et al. | |
| 2002/0134394 A1 | 9/2002 | Baskevitch et al. | |
| 2002/0174874 A1 | 11/2002 | Williams | |
| 2003/0056801 A1 | 3/2003 | Krauss et al. | |
| 2004/0025891 A1 | 2/2004 | McAdam et al. | |
| 2005/0034365 A1 | 2/2005 | Li et al. | |
| 2005/0072047 A1 | 4/2005 | Conkling et al. | |
| 2005/0121046 A1 | 6/2005 | Hempfling et al. | |
| 2005/0175991 A1 | 8/2005 | Sulakvelidze et al. | |
| 2009/0246336 A1 | 10/2009 | Burnett et al. | |
| 2009/0308121 A1 | 12/2009 | Reddy et al. | |
| 2010/0068185 A1 | 3/2010 | Reber | |
| 2010/0166709 A1 | 7/2010 | Kang et al. | |
| 2011/0239324 A1 | 9/2011 | Davenport et al. | |
| 2012/0065069 A1* | 3/2012 | Yang ..................... A01G 7/06 504/138 |
| 2013/0269719 A1 | 10/2013 | Marshall et al. | |
| 2014/0030382 A1 | 1/2014 | Ter Haar et al. | |
| 2014/0261478 A1* | 9/2014 | Xu ....................... C07K 14/005 131/290 |
| 2014/0299136 A1* | 10/2014 | Moldoveanu ........ A24B 15/183 131/290 |
| 2014/0308246 A1* | 10/2014 | Tolmasky ................ C12N 9/80 424/93.2 |

FOREIGN PATENT DOCUMENTS

| | | | |
|---|---|---|---|
| EP | 0070112 | 1/1983 | |
| EP | 0128954 | 12/1984 | |
| EP | 0144474 | 6/1985 | |
| JP | 62123104 | 6/1987 | |
| JP | 2001158710 | 6/2001 | |
| WO | WO-2006034554 A1 * | 4/2006 | ............... C12N 7/00 |

OTHER PUBLICATIONS

"Tobacco Leaf Harvesting, Curing, and Fermenting", Leaf Only, 2009, accessed at leafonly.com on Mar. 8, 2017.*
"In Situ", Random House Dictionary, 2017, accessed at dictionary.com on Mar. 9, 2017.*
"Bacteriophages", American Heritage Dictionary of the English Language, Fifth Edition, 2016, Houghton Mifflin Harcourt Publishing Company, accessed at thefreedictionary.com on Mar. 8, 2017.*
"Anatomy of a Cigarette", NOVA Online, 2001, accesed at pbs.org on Mar. 17, 2017.*

(Continued)

*Primary Examiner* — Edmund H Lee
*Assistant Examiner* — Jamel M Nelson
(74) *Attorney, Agent, or Firm* — Middleton Reutlinger

(57) ABSTRACT

Disclosed is a process for inhibiting formation of nitrosamines by bacteria in tobacco, comprising contacting the tobacco with a substance comprising a plurality of bacteriophages capable of lysing bacteria that form nitrosamines. Disclosed also is a tobacco product possessing a diminished concentration of nitrosamines.

13 Claims, No Drawings

(56) References Cited

OTHER PUBLICATIONS

Tanaka, H.; Control of tobacco bacterial wilt by an avirulent strain of Pseudomonas solanacearum M4S and its bacteriophage; Annals of the Pyhtophthological Society of Japan; vol. 56 No. 2 pp. 243-246; 1990; JP Dec. 31, 1990.
Brunnemann et al.; Formation and Analysis of Tobacco-Specific NNitrosamines; vol. 26, No. 2; 1996; US Dec. 31, 1996.
Jones, et al.; Bacteria-invading Virus Yields New Discoveries; Jan. 10, 2014; US.

\* cited by examiner

PROCESS FOR INHIBITING FORMATION OF NITROSAMINES

CROSS-REFERENCE TO RELATED APPLICATIONS

The present application claims priority on the basis of U.S. provisional application Ser. No. 61/994,193, filed May 16, 2014, which is hereby incorporated by reference.

FIELD OF THE INVENTION

A process such as is described in various embodiments herein relates to growing, harvesting and/or treating plants, and, in particular, tobacco plants, that is, plants belonging to any one or more species of genus *Nicotiana*, from which are made or derived products intended for human consumption. Accordingly, a process such as is described in various embodiments herein relates to growing, harvesting and/or treating plants so that one or more products made or derived from such plants possess one or more desired and favorable properties.

BACKGROUND OF THE INVENTION

Popular smoking articles, such as cigarettes, have a substantially cylindrical rod shaped structure and include a charge, roll or column of smokable material such as shredded tobacco (e.g., in cut filler form) surrounded by a paper wrapper thereby forming a so-called "tobacco rod." Normally, a cigarette has a cylindrical filter element aligned in an end-to-end relationship with the tobacco rod. Typically, a filter element comprises plasticized cellulose acetate tow circumscribed by a paper material known as "plug wrap." Certain cigarettes incorporate a filter element having multiple segments, and one of those segments can comprise activated charcoal particles. Typically, the filter element is attached to one end of the tobacco rod using a circumscribing wrapping material known as "tipping paper." It also has become desirable to perforate the tipping material and plug wrap, in order to provide dilution of drawn mainstream smoke with ambient air. A cigarette is employed by a smoker by lighting one end thereof and burning the tobacco rod. The smoker then receives mainstream smoke into his/her mouth by drawing on the opposite end (e.g., the filter end) of the cigarette.

The tobacco used for cigarette manufacture is typically used in blended form. For example, certain popular tobacco blends, commonly referred to as "American blends," comprise mixtures of flue-cured tobacco, burley tobacco, and Oriental tobacco, and in many cases, certain processed tobaccos, such as reconstituted tobacco and processed tobacco stems. The precise amount of each type of tobacco within a tobacco blend used for the manufacture of a particular cigarette brand varies from brand to brand. However, for many tobacco blends, flue-cured tobacco makes up a relatively large proportion of the blend, while Oriental tobacco makes up a relatively small proportion of the blend. See, for example, Tobacco Encyclopedia, Voges (Ed.) p. 44-45 (1984), Browne, The Design of Cigarettes, 3rd Ed., p. 43 (1990) and Tobacco Production, Chemistry and Technology, Davis et al. (Eds.) p. 346 (1999).

Through the years, various treatment methods and additives have been proposed for altering the overall character or nature of tobacco materials utilized in tobacco products. For example, additives or treatment processes have been utilized in order to alter the chemistry or sensory properties of the tobacco material, or in the case of smokable tobacco materials, to alter the chemistry or sensory properties of mainstream smoke generated by smoking articles including the tobacco material. The sensory attributes of cigarette smoke can be enhanced by incorporating flavoring materials into various components of a cigarette. Exemplary flavoring additives include menthol and products of Maillard reactions, such as pyrazines, aminosugars, and Amadori compounds. See also, Leffingwell et al., Tobacco Flavoring for Smoking Products, R.J. Reynolds Tobacco Company (1972), which is incorporated herein by reference. In some cases, treatment processes involving the use of heat can impart to the processed tobacco a desired color or visual character, desired sensory properties, or a desired physical nature or texture. Various processes for preparing flavorful and aromatic compositions for use in tobacco compositions are set forth in U.S. Pat. No. 3,424,171 to Rooker; U.S. Pat. No. 3,476,118 to Luttich; U.S. Pat. No. 4,150,677 to Osborne, Jr. et al.; U.S. Pat. No. 4,986,286 to Roberts et al.; U.S. Pat. No. 5,074,319 to White et al.; U.S. Pat. No. 5,099,862 to White et al.; U.S. Pat. No. 5,235,992 to Sensabaugh, Jr.; U.S. Pat. No. 5,301,694 to Raymond et al.; U.S. Pat. No. 6,298,858 to Coleman, III et al.; U.S. Pat. No. 6,325,860 to Coleman, III et al.; U.S. Pat. No. 6,428,624 to Coleman, III et al.; U.S. Pat. No. 6,440,223 to Dube et al.; U.S. Pat. No. 6,499,489 to Coleman, III; U.S. Pat. No. 6,591,841 to White et al.; and U.S. Pat. No. 6,695,924 to Dube et al.; and US Pat. Appl. Publication Nos. 2004/0173228 to Coleman, III; 2010/0037903 to Coleman, III et al.; and 2013/0014771 to Coleman, III et al., each of which is incorporated herein by reference. Additionally, examples of representative components that can be employed as so-called natural tar diluents in tobacco products are set in PCT WO 07/012980 to Lipowicz, which is incorporated herein by reference.

Tobacco also may be enjoyed in a so-called "smokeless" form. Particularly popular smokeless tobacco products are employed by inserting some form of processed tobacco or tobacco-containing formulation into the mouth of the user. Various types of smokeless tobacco products are set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,987,907 to Townsend; U.S. Pat. No. 5,092,352 to Sprinkle, III et al.; U.S. Pat. No. 5,387,416 to White et al.; and U.S. Pat. No. 8,336,557 to Kumar et al.; US Pat. Appl. Pub. Nos. 2005/0244521 to Strickland et al. and 2008/0196730 to Engstrom et al.; PCT WO 04/095959 to Arnarp et al.; PCT WO 05/063060 to Atchley et al.; PCT WO 05/016036 to Bjorkholm; and PCT WO 05/041699 to Quinter et al., each of which is incorporated herein by reference. See, for example, the types of smokeless tobacco formulations, ingredients, and processing methodologies set forth in U.S. Pat. No. 6,953,040 to Atchley et al. and U.S. Pat. No. 7,032,601 to Atchley et al., each of which is incorporated herein by reference.

One type of smokeless tobacco product is referred to as "snuff." Representative types of moist snuff products, commonly referred to as "snus," have been manufactured in Europe, particularly in Sweden, by or through companies such as Swedish Match AB, Fiedler & Lundgren AB, Gustavus AB, Skandinavisk Tobakskompagni A/S, and Rocker Production AB. Snus products available in the U.S.A. have been marketed under the tradenames Camel Snus Frost, Camel Snus Original and Camel Snus Spice by R. J. Reynolds Tobacco Company. See also, for example, Bryzgalov et al., 1N1800 Life Cycle Assessment, Comparative Life Cycle Assessment of General Loose and Portion Snus (2005). In addition, certain quality standards associated with snus manufacture have been assembled as a so-called GothiaTek standard. Representative smokeless tobacco products also have been marketed under the tradenames Oliver Twist by House of Oliver Twist A/S; Copenhagen, Skoal, SkoalDry, Rooster, Red Seal, Husky, and Revel by U.S. Smokeless Tobacco Co.; "taboka" by Philip Morris USA; Levi Garrett, Peachy, Taylor's Pride, Kodiak, Hawken Wintergreen, Grizzly, Dental, Kentucky King, and Mammoth Cave by Conwood Company, LLC; and Camel Orbs, Camel Sticks, and Camel Strips by R. J. Reynolds Tobacco Company.

The sensory attributes of smokeless tobacco can also be enhanced by incorporation of certain flavoring materials. See, for example, U.S. Pat. No. 6,668,839 to Williams; U.S. Pat. No. 6,834,654 to Williams; U.S. Pat. No. 7,032,601 to Atchley et al.; U.S. Pat. No. 7,694,686 to Atchley et al.; U.S. Pat. No. 7,861,728 to Holton, Jr. et al.; U.S. Pat. No. 7,819,124 to Strickland et al.; U.S. Pat. No. 7,810,507 to Dube et al.; and U.S. Pat. No. 8,168,855 to Nielsen et al; US Pat. Appl. Pub. Nos. 2004/0020503 to Williams, 2006/0191548 to Strickland et al.; 2007/0062549 to Holton, Jr. et al.; 2008/0029116 to Robinson et al.; 2008/0029117 to Mua et al.; and 2008/0173317 to Robinson et al., each of which is incorporated herein by reference.

Nitrosamines are known to be present in air, foods, beverages, cosmetics, and even pharmaceuticals. Preussman et al., Chemical Carcinogens, 2.sup.nd Ed., Vol. 2, Searle (Ed.) ACS Monograph 182, 829-868 (1984). Tobacco and tobacco smoke also are known to contain nitrosamines. Green et al., Rec. Adv. Tob. Sci., 22, 131 (1996). Tobacco is known to contain a class of nitrosamines known as tobacco specific nitrosamines (TSNA). Hecht, Chem. Res. Toxicol., 11(6), 559-603 (1998); Hecht, Mut. Res., 424(1,2), 127-142 (1999). TSNA have been reported to be present in smokeless tobacco, Brunnemann et al., Canc. Lett., 37, 7-16 (1987), Tricker, Canc. Lett., 42, 113-118 (1988), Andersen et al., Canc. Res., 49, 5895-5900 (1989); cigarette smoke, Spiegelhalder et al., Euro. J. Canc. Prey., 5(1), 33-38 (1996); Hoffman et al., J. Toxicol. Env. Hlth., 50, 307-364 (1997); Borgerding et al., Food Chem. Toxicol., 36, 169-182 (1997); nicotine-containing gum, Osterdahl, Food Chem. Toxic., 28(9), 619-622 (1990); and nicotine-containing transdermal patch, Adlkofer, In: Clarke et al. (Eds.), Effects of Nicotine on Biological Systems II, 17-25 (1995).

Green and freshly harvested tobaccos have been reported to be virtually free of TSNA. Parsons, Tob. Sci., 30, 81-82 (1986); Spiegelhalder et al., Euro. J. Canc. Prey., 5(1), 33-38 (1996); Brunnemann et al., J. Toxicol.-Clin. Toxicol., 19(6&7), 661-668 (1982-3); Andersen et al., J. Agric. Food Chem., 37(1), 44-50 (1989); Djordjevic et al., J. Agric. Food Chem., 37, 752-756 (1989). However, it has been observed that TSNA form during the post-harvest processing to which tobacco is subjected. Tricker, Canc. Lett., 42, 113-118 (1988); Chamberlain et al., J. Agric. Food Chem., 36, 48-50 (1988). TSNA are recognized as being formed when tobacco alkaloids, such as nicotine, are nitrosated. Hecht, Chem. Res. Toxicol., 11(6), 559-603 (1998). There has been considerable effort expended toward studying the mechanism of formation of TSNA.

Significant efforts have been expended towards studying the mechanism of TSNA formation during tobacco curing, particularly for Burley tobacco. As a result, it has been postulated that TSNA form during the air-curing of Burley tobacco as a result of microbial mediated conversion of nitrate to nitrite, and the subsequent reaction of nitrate-derived chemical species with alkaloids present in the tobacco. Hamilton et al., Tob. Sci., 26, 133-137 (1982); Burton et al., J. Agric. Food Chem., 40, 1050-1055 (1992); Bush et al., Coresta Bulletin Information, Abstract 9814 (1995); Wiernik et al., Rec. Adv. Tob. Sci., 21, 39-80 (1995); Cui et al., TCRC (1996). It also has been suggested that the mechanism by which TSNA form during the flue-curing of Virginia tobaccos is similar to that mechanism postulated for air-cured Burley tobacco. See, Djordjevic et al., J. Agric. Food Chem., 37, 752-756 (1989) and Peele et al., Coresta Bulletin Information, Abstract 9822 (1995). See also, PCT WO 98/05226 and PCT WO 98/58555, and U.S. Pat. No. 5,803,801 to O'Donnell et at.

Because tobacco has long been cultivated and tobacco products have accordingly long been made, yet with formation of nitrosamines in tobacco and tobacco products on many occasions and in many circumstances occurring, limiting the usefulness of such tobacco and tobacco products, there is a long-felt need for a process for inhibiting formation of nitrosamines in tobacco and tobacco products.

SUMMARY OF EMBODIMENTS

A process such as is described in various embodiments herein provides a process for treating a plant or a portion thereof to modify the amount of certain nitrosamine compounds present therein. Plants to which a process such as is described in various embodiments herein can be applied can vary, and include without limitation any flowering plants or conifers, including various types of vines, trees, bushes, and other plants, such as those that bear fruit, vegetables, and legumes, as well as grains.

In an aspect, a process such as is described in various embodiments herein involves taking a plant that is used to produce a commodity, particularly a plant used as a source of food or other oral products, and treating the plant to modify the amount of certain nitrosamine compounds present in that part of the plant that is harvested and/or otherwise processed for oral consumption. Plants to which the methods can be applied include, but are not limited to, vegetable plants such as beans (e.g., lima beans, green beans, soy beans, coffee beans), cabbage, okra, squash, lettuce, tomatoes, peppers, asparagus, celery, and the like; root and bulb vegetables (e.g., radishes, onions, garlic, and carrots); grains (e.g., wheat, barley, oats, corn, rice, rye, sorghum); fruit-bearing plants (e.g., strawberries); fruit-bearing vines (e.g., grapes, melons, and cranberries); fruit-bearing bushes (e.g., blueberries) and fruit-bearing trees (e.g., fruits such as oranges, lemons, limes, grapefruits, cherries, peaches, bananas, plantains, and apples); legumes (e.g., nuts); tea; hops; and herbs and spice plants. In certain embodiments, a process such as is described in various embodiments herein relates to tobacco.

In an aspect, a process such as is described in various embodiments herein can relate to modifying (e.g., decreasing) the content of one or more nitrosamine compounds in a tobacco material, comprising contacting an unharvested tobacco plant or portion thereof with one or more bacteriophages. In some embodiments, the unharvested tobacco plant or portion thereof is selected from the group consisting of a tobacco seed, a tobacco seedling, an immature live plant, a mature live plant, or a portion thereof.

In an aspect, a process such as is described in various embodiments herein can relate to modifying (e.g., decreasing) the content of one or more nitrosamine compounds in a tobacco material, comprising contacting a harvested tobacco plant or portion thereof with one or more bacteriophages. In some embodiments, the harvested tobacco plant or portion thereof is selected from the group consisting of a tobacco seed, a tobacco plant, a tobacco leaf, a tobacco stem, or a portion thereof.

In an aspect, a process such as is described in various embodiments herein can relate to modifying (e.g., decreasing) the content of one or more nitrosamine compounds in a tobacco material, comprising contacting a curing tobacco plant or portion thereof with one or more bacteriophages. In some embodiments, the curing tobacco plant or portion thereof is selected from the group consisting of a tobacco seed, a tobacco plant, a tobacco leaf, a tobacco stem, or a portion thereof.

In an aspect, a process such as is described in various embodiments herein can relate to modifying (e.g., decreasing) the activity of one or more nitrate-reducing enzymes in or on a tobacco material, comprising contacting an unharvested tobacco plant or portion thereof, a harvested tobacco plant or portion thereof, or a curing tobacco plant or portion thereof with one or more bacteriophages.

When used in connection with a process such as is described in various embodiments herein, a "nitrate-reducing enzyme" is an oxidoreductase capable of electrochemically reducing nitrate as a substrate. A catalytic cycle of such an enzyme can also concomitantly electrochemically oxidize another substrate (that is, a substrate other than nitrate) or a cofactor. A nitrate-reducing enzyme can be categorized within EC 1.7 per recommendation of the Nomenclature Committee of the International Union of Biochemistry and Molecular Biology, and can be within any of EC 1.7.1, EC 1.7.2, EC 1.7.3, EC 1.7.5, EC 1.7.6, EC 1.7.7 or EC 1.7.99.

In an aspect, a process such as is described in various embodiments herein can relate to modifying (e.g., decreasing) the number of one or more microorganisms in or on a tobacco material, comprising contacting an unharvested tobacco plant or portion thereof, a harvested tobacco plant or portion thereof, or a curing tobacco plant or portion thereof with one or more bacteriophages.

The bacteriophage or bacteriophages contacted according to a process such as is described in various embodiments herein can vary and different bacteriophages can, in some embodiments, effect the decrease in number of different nitrosamine compounds in or on the tobacco material (e.g., the tobacco plant or portion thereof).

The bacteriophage or bacteriophages contacted according to a process such as is described in various embodiments herein can vary and different bacteriophages can, in some embodiments, effect the decrease in activity of different nitrate-reducing enzymes in or on the tobacco material (e.g., the tobacco plant or portion thereof).

The bacteriophage or bacteriophages contacted according to a process such as is described in various embodiments herein can vary and different bacteriophages can, in some embodiments, effect the decrease in number of different microorganisms in or on the tobacco material (e.g., the tobacco plant or portion thereof).

The contacting step can, in some embodiments, comprise applying the one or more bacteriophages in a solution, suspension, or dispersion in water. A process such as is described in various embodiments herein can further comprise additional steps, including, but not limited to, harvesting the unharvested tobacco plant or portion thereof and/or applying one or more probiotic bacteria, probiotic yeasts, or a combination thereof to the unharvested or harvested tobacco plant or portion thereof and/or incorporating the tobacco material into a smokeless tobacco product or a smoking article. The form of the tobacco material can, in some embodiments, be in the form of cut filler or in the form of a tobacco blend.

In another aspect of a process such as is described in various embodiments herein is provided a tobacco product in the form of a cigarette or a smokeless tobacco product prepared by modifying (e.g., decreasing) the content of one or more nitrosamine compounds in a tobacco material, comprising contacting an unharvested tobacco plant or portion thereof with one or more bacteriophages according to the method described herein; processing the harvested tobacco plant or portion thereof to provide a tobacco material in a form suitable for incorporation in a tobacco product; and incorporating the tobacco material into a smokeless tobacco product or a smoking article. The smoking article thus produced can be, for example, in the form of a cigarette. Accordingly, in one embodiment is provided a tobacco product in the form of a smoking article or a smokeless tobacco product, the tobacco product comprising a tobacco composition, wherein the tobacco composition comprises a bacteriophage-treated tobacco material.

A process such as is described in various embodiments herein provides materials from *Nicotiana* species (e.g., tobacco-derived materials) comprising isolated components from plants of the *Nicotiana* species useful for incorporation into tobacco compositions utilized in a variety of tobacco products, such as smoking articles and smokeless tobacco products, or more generally into compositions that may comprise a flavorant. A process such as is described in various embodiments herein also provides processes for isolating components from *Nicotiana* species (e.g., tobacco materials), and processes for processing those components and tobacco materials incorporating those components. For example, tobacco-derived materials can be prepared by subjecting at least a portion of a tobacco plant (e.g., leaves, stalks, roots, or stems) to a separation process, which typically can include multiple sequential extraction steps, in order to isolate desired components of the tobacco material. For example, tobacco-derived materials can be prepared by subjecting at least a portion of a tobacco plant (e.g., leaves, stalks, roots, or stems) to a separation process, which typically can include multiple sequential extraction steps, in order to isolate desired components of the tobacco material.

When used in connection with a process such as is described in various embodiments herein, the term "biomass" denotes any one or more portions of a plant, and in particular denotes substantially the entirety of the superterranean portion of a plant, optionally including some or all of the subterranean portion of a plant. Accordingly, the term "biomass" may refer to flower or to leaf or to seed or to any other superterranean portion of a plant, or to any combination thereof, optionally including some or all of the subterranean portion of a plant. Accordingly, the term "biomass" and related terms such as "biomatter" and "plant source" may be properly understood to refer to any one or more portions of a harvested plant that may be processed to extract, separate, or isolate components of interest therefrom.

When used in connection with a process such as is described in various embodiments herein, the term "one or more plants of genus *Nicotiana*" denotes any one or more plants of the genus *Nicotiana* of family Solanaceae, including, for example, any one or more of the following: *N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata,* and *N.* x *sanderae, N. afri-* cana, *N. amplexicaulis*, *N. benavidesii*, *N. bonariensis*, *N. debneyi*, *N. longiflora*, *N. maritina*, *N. megalosiphon*, *N. occidentalis*, *N. paniculata*, *N. plumbaginifolia*, *N. raimondii*, *N. rosulata*, *N. rustica*, *N. simulans*, *N. stocktonii*, *N. suaveolens*, *N. tabacum*, *N. umbratica*, *N. velutina*, and *N. wigandioides*, *N. acaulis*, *N. acuminata*, *N. attenuata*, *N. benthamiana*, *N. cavicola*, *N. clevelandii*, *N. cordifolia*, *N. corymbosa*, *N. fragrans*, *N. goodspeedii*, *N. linearis*, *N. miersii*, *N. nudicaulis*, *N. obtusifolia*, *N. occidentalis* subsp. *Hersperis*, *N. pauciflora*, *N. petunioides*, *N. quadrivalvis*, *N. repanda*, *N. rotundifolia*, *N. solanifolia*, *N. spegazzinii*.

The use of *Nicotiana*-derived (e.g., tobacco-derived) materials produced by a process such as is described in various embodiments herein enables the preparation of tobacco compositions for smoking articles or smokeless tobacco compositions that are derived substantially or even entirely from *Nicotiana* materials. For example, a tobacco composition can incorporate tobacco or tobacco-derived material of some form, including isolated components from *Nicotiana* species, such that at least about 80 weight percent, more typically at least about 90 weight percent, or even at least about 95 weight percent (on a dry weight basis), of that tobacco composition consists of tobacco-derived material.

DETAILED DESCRIPTION

A process such as is described in various embodiments herein now will be described more fully hereinafter. A process such as is described in various embodiments herein may, however, be embodied in many different forms and should not be construed as limited to the embodiments set forth herein; rather, these embodiments are provided so that this disclosure will be thorough and complete, and will fully convey the scope of a process such as is described in various embodiments herein to those skilled in the art. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). When used in this specification and the claims as an adverb rather than a preposition, "about" means "approximately" and comprises the stated value and every value within 10% of that value; in other words, "about 100%" includes 90% and 110% and every value in between.

The selection of the plant from a *Nicotiana* species can vary; and in particular, the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and Rustica tobaccos, as well as various other rare or specialty tobaccos. Descriptions of various types of tobaccos, growing practices and harvesting practices are set forth in Tobacco Production, Chemistry and Technology, Davis et al. (Eds.) (1999), which is incorporated herein by reference. Various representative types of plants from the Nicotiana species are set forth in Goodspeed, The Genus *Nicotiana* (Chronica Botanica, 1954); U.S. Pat. No. 4,660,577 to Sensabaugh, Jr. et al.; U.S. Pat. No. 5,387,416 to White et al.; U.S. Pat. No. 7,025,066 to Lawson et al.; U.S. Pat. No. 7,798,153 to Lawrence, Jr.; and U.S. Pat. No. 8,186,360 to Marshall et al., each of which is incorporated herein by reference. Of particular interest are *N. alata*, *N. arentsii*, *N. excelsior*, *N. forgetiana*, *N. glauca*, *N. glutinosa*, *N. gossei*, *N. kawakamii*, *N. knightiana*, *N. langsdorffi*, *N. otophora*, *N. setchelli*, *N. sylvestris*, *N. tomentosa*, *N. tomentosiformis*, *N. undulata*, and *N.* x *sanderae*. Also of interest are *N. africana*, *N. amplexicaulis*, *N. benavidesii*, *N. bonariensis*, *N. debneyi*, *N. longiflora*, *N. maritina*, *N. megalosiphon*, *N. occidentalis*, *N. paniculata*, *N. plumbaginifolia*, *N. raimondii*, *N. rosulata*, *N. rustica*, *N. simulans*, *N. stocktonii*, *N. suaveolens*, *N. tabacum*, *N. umbratica*, *N. velutina*, and *N. wigandioides*. Other plants from the *Nicotiana* species include *N. acaulis*, *N. acuminata*, *N. attenuata*, *N. benthamiana*, *N. cavicola*, *N. clevelandii*, *N. cordifolia*, *N. corymbosa*, *N. fragrans*, *N. goodspeedii*, *N. linearis*, *N. miersii*, *N. nudicaulis*, *N. obtusifolia*, *N. occidentalis* subsp. *hersperis*, *N. pauciflora*, *N. petunioides*, *N. quadrivalvis*, *N. repanda*, *N. rotundifolia*, *N. solanifolia* and *N. spegazzinii*.

*Nicotiana* species can be derived using genetic-modification or crossbreeding techniques (e.g., tobacco plants can be genetically engineered or crossbred to increase or decrease production of certain components or to otherwise change certain characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al.; and U.S. Pat. No. 7,230,160 to Benning et al.; US Patent Appl. Pub. No. 2006/0236434 to Conkling et al.; and PCT WO 08/103935 to Nielsen et al.

For the preparation of smokeless and smokable tobacco products, it is typical for harvested plants of a *Nicotiana* species to be subjected to a curing process. Descriptions of various types of curing processes for various types of tobaccos are set forth in Tobacco Production, Chemistry and Technology, Davis et al. (Eds.) (1999). Exemplary techniques and conditions for curing flue-cured tobacco are set forth in Nestor et al., Beitrage Tabakforsch. Int., 20, 467-475 (2003) and U.S. Pat. No. 6,895,974 to Peele, which are incorporated herein by reference. See, also, for example, U.S. Pat. No. 7,650,892 to Groves et al., which is incorporated herein by reference. Representative techniques and conditions for air curing tobacco are set forth in Roton et al., Beitrage Tabakforsch. Int., 21, 305-320 (2005) and Staaf et al., Beitrage Tabakforsch. Int., 21, 321-330 (2005), which are incorporated herein by reference. Certain types of tobaccos can be subjected to alternative types of curing processes, such as fire curing or sun curing. Preferably, harvested tobaccos that are cured are then aged.

At least a portion of the plant of a *Nicotiana* species (e.g., at least a portion of the tobacco portion) can be employed in an immature form. That is, the plant, or at least one portion of that plant, can be harvested before reaching a stage normally regarded as ripe or mature. As such, for example, tobacco can be harvested when the tobacco plant is at the point of a sprout, is commencing leaf formation, is commencing seeding, is commencing flowering, or the like.

At least a portion of the plant of a *Nicotiana* species (e.g., at least a portion of the tobacco portion) can be employed in a mature form. That is, the plant, or at least one portion of that plant, can be harvested when that plant (or plant portion) reaches a point that is traditionally viewed as being ripe, over-ripe or mature. As such, for example, through the use of tobacco harvesting techniques conventionally employed by farmers, Oriental tobacco plants can be harvested, burley tobacco plants can be harvested, or Virginia tobacco leaves can be harvested or primed by stalk position. After harvest, a plant of a *Nicotiana* species, or portion thereof, can be used in a green form (e.g., tobacco can be used without being subjected to any curing process). For example, tobacco in green form can be frozen, freeze-dried, subjected to irradiation, yellowed, dried, cooked (e.g., roasted, fried or boiled), or otherwise subjected to storage or treatment for later use. Such tobacco also can be subjected to aging conditions.

In accordance with a process such as is described in various embodiments herein, a tobacco product may incorporate tobacco that is combined with some form of biomass or one or more anatomical parts obtained from, or derived from, a plant of at least one *Nicotiana* species. That is, a portion of a tobacco product according to a process such as is described in various embodiments herein can be composed of some form of biomass or one or more anatomical parts of a *Nicotiana* species, such as parts or pieces of biomass or one or more anatomical parts, or processed materials incorporating processed biomass or one or more anatomical parts or components thereof. At least a portion of the tobacco product can be composed of components of biomass or one or more anatomical parts, such as ingredients removed from biomass or one or more anatomical parts (e.g., by extraction, distillation, or other types of processing techniques). At least a portion of the tobacco product can be composed of components derived from biomass or one or more anatomical parts, such as components collected after subjecting biomass or one or more anatomical parts to chemical reaction or after subjecting components collected from biomass or one or more anatomical parts to chemical reaction (e.g., acid/base reaction conditions or enzymatic treatment).

A *Nicotiana* species can be selected for the type of biomass or anatomical part that it produces. For example, plants can be selected on the basis that those plants produce relatively abundant biomass or seed, produce biomass or seed that incorporate relatively high levels of specific desired components, and the like.

A *Nicotiana* species of plant can be grown under agronomic conditions so as to promote development of biomass or one or more anatomical parts. Tobacco plants can be grown in greenhouses, growth chambers, or outdoors in fields, or grown hydroponically.

According to a process such as is described in various embodiments herein, biomass or one or more anatomical parts are harvested from a *Nicotiana* species of plant. The manner by which biomass or one or more anatomical parts are harvested can vary. Typically, essentially all the biomass or anatomical parts can be harvested, and employed as such.

Time of harvest during the life cycle of the plant can vary. For example, biomass or one or more anatomical parts can be harvested when immature. Alternatively, biomass or one or more anatomical parts can be harvested after the point that the plant has reached maturity.

Post-harvest processing of biomass or one or more anatomical parts can vary. After harvest, the biomass or one or more anatomical parts, or portion thereof, can be used in the harvested form (e.g., the biomass or one or more anatomical parts, or portion thereof, can be used without being subjected to any curing and/or aging process steps). For example, biomass or one or more anatomical parts can be used without being subjected to significant storage, handling or processing conditions. In certain situations, it is preferable that fresh biomass or one or more anatomical parts be used virtually immediately after harvest. Alternatively, for example, biomass or one or more anatomical parts can be refrigerated or frozen for later use, freeze dried, subjected to irradiation, yellowed, dried, cured (e.g., using air drying techniques or techniques that employ application of heat), heated or cooked (e.g., roasted, fried or boiled), or otherwise subjected to storage or treatment for later use.

Harvested biomass can be physically processed. Biomass or one or more anatomical parts, or one or more parts thereof, can be further subdivided into parts or pieces (e.g., biomass can be comminuted, pulverized, milled or ground into pieces or parts that can be characterized as granules, particulates or fine powders, or, e.g., petals can be removed from remaining portion of a flower). Biomass or one or more anatomical parts, or one or more parts thereof, can be subjected to external forces or pressure (e.g., by being pressed or subjected to roll treatment). When carrying out such processing conditions, biomass or one or more anatomical parts can have a moisture content that approximates its natural moisture content (e.g., its moisture content immediately upon harvest), a moisture content achieved by adding moisture to the biomass, or a moisture content that results from the drying of the biomass. For example, powdered, pulverized, ground or milled pieces of biomass or one or more anatomical parts can have moisture contents of less than about 25 weight percent, often less than about 20 weight percent, and frequently less than about 15 weight percent. Parts or pieces of biomass or one or more anatomical parts can be used as components of tobacco products without further processing, or alternatively the particulate biomass or anatomical part material can be processed further prior to incorporation into a tobacco product.

Harvested biomass or one or more anatomical parts or components thereof can be subjected to other types of processing conditions. For example, components of biomass or one or more anatomical parts can be separated from one another, or otherwise fractionated into chemical classes or mixtures of individual compounds. As used herein, an "isolated biomass component," "isolated component of one or more anatomical parts," "biomass isolate," "isolate of one or more anatomical parts," or "isolate" when used as a noun is a compound or complex mixture of compounds separated from biomass or one or more anatomical parts of a plant of a *Nicotiana* species. The isolated biomass component or isolated component of one or more anatomical parts can be a single compound, a homologous mixture of similar compounds (e.g., isomers of a flavorful or aromatic compound), or a heterologous mixture of dissimilar compounds (e.g., a complex mixture of various compounds of different types, preferably having desirable sensory attributes).

Typical separation processes can include one or more process steps such as solvent extraction (e.g., using polar solvents, non-polar organic solvents, or supercritical fluids), chromatography, distillation, filtration, cold pressing or other pressure-based techniques, recrystallization, and/or solvent-solvent partitioning. Exemplary extraction and separation solvents or carriers include water, alcohols (e.g., methanol or ethanol), hydrocarbons (e.g., heptane and hexane), diethyl ether, methylene chloride and supercritical carbon dioxide. Exemplary techniques useful for extracting components from Nicotiana species are described in U.S. Pat. No. 4,144,895 to Fiore; U.S. Pat. No. 4,150,677 to Osborne, Jr. et al.; 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, each of which is incorporated herein by reference. See also, the types of separation techniques set forth in Brandt et al., LC-GC Europe, p. 2-5 (Mar. 2002) and Wellings, A Practical Handbook of Preparative HPLC (2006), which are incorporated herein by reference. In addition, the biomass or components thereof can be subjected to the types of treatments set forth in Ishikawa et al., Chem. Pharm. Bull., 50, 501-507 (2002); Tienpont et al., Anal. Bioanal. Chem., 373, 46-55 (2002); Ochiai, Gerstel Solutions Worldwide, 6, 17-19 (2006); Coleman, III, et al., J. Sci. Food and Agric., 84, 1223-1228 (2004); Coleman, III et al., J. Sci. Food and Agric., 85, 2645-2654 (2005); Pawliszyn, ed., Applications of Solid Phase Microextraction, RSC Chromatography Monographs, (Royal Society of Chemistry, UK) (1999); Sahraoui et al., J. Chrom., 1210, 229-233 (2008); and U.S. Pat. No. 5,301,694 to Raymond et al., each of which is incorporated herein by reference. See also, for example, the types of processing techniques set forth in Frega et al., JAOCS, 68, 29-33 (1991); Patel et al., Tob. Res., 24, 44-49 (1998); Giannelos et al., Ind. Crops Prod., 16, 1-9 (2002); Mukhtar et al., Chinese J. Chem., 25, 705-708 (2007); and Stanisavljevic et al., Eur. J. Lipid Sci. Technol., 111, 513-518 (2009), each of which is incorporated herein by reference.

A portion of a harvested tobacco plant can be employed in any of a variety of forms. Harvested biomass or one or more anatomical parts can be employed as a component of processed tobaccos. In one regard, harvested biomass or one or more anatomical parts can be employed within a casing formulation for application to tobacco strip (e.g., using the types of manners and methods set forth in U.S. Pat. No. 4,819,668 to Shelar, which is incorporated herein by reference) or within a top dressing formulation. Alternatively, harvested biomass or one or more anatomical parts can be employed as an ingredient of a reconstituted tobacco material (e.g., using the types of tobacco reconstitution processes generally set forth in U.S. Pat. No. 5,143,097 to Sohn; U.S. Pat. No. 5,159,942 to Brinkley et al.; U.S. Pat. No. 5,598,868 to Jakob; U.S. Pat. No. 5,715,844 to Young; U.S. Pat. No. 5,724,998 to Gellatly; and U.S. Pat. No. 6,216,706 to Kumar, which are incorporated herein by reference). Harvested biomass or one or more anatomical parts also can be incorporated into a cigarette filter (e.g., in the filter plug, plug wrap, or tipping paper) or incorporated into cigarette wrapping paper, preferably on the inside surface, during the cigarette manufacturing process.

Harvested biomass or one or more anatomical parts can be incorporated into smoking articles. Representative tobacco blends, non-tobacco components, and representative cigarettes manufactured therefrom, are set forth in U.S. Pat. No. 4,836,224 to Lawson et al.; U.S. Pat. No. 4,924,888 to Perfetti et al.; U.S. Pat. No. 5,056,537 to Brown et al.; U.S. Pat. No. 5,220,930 to Gentry; and U.S. Pat. No. 5,360,023 to Blakley et al.; US Pat. Application 2002/0000235 to Shafer et al.; and PCT WO 02/37990. Those tobacco materials also can be employed for the manufacture of those types of cigarettes that are described in U.S. Pat. No. 4,793,365 to Sensabaugh; U.S. Pat. No. 4,917,128 to Clearman et al.; U.S. Pat. No. 4,947,874 to Brooks et al.; U.S. Pat. No. 4,961,438 to Korte; U.S. Pat. No. 4,920,990 to Lawrence et al.; U.S. Pat. No. 5,033,483 to Clearman et al.; U.S. Pat. No. 5,074,321 to Gentry et al.; U.S. Pat. No. 5,105,835 to Drewett et al.; U.S. Pat. No. 5,178,167 to Riggs et al.; U.S. Pat. No. 5,183,062 to Clearman et al.; U.S. Pat. No. 5,211,684 to Shannon et al.; U.S. Pat. No. 5,247,949 to Deevi et al.; U.S. Pat. No. 5,551,451 to Riggs et al.; U.S. Pat. No. 5,285,798 to Banerjee et al.; U.S. Pat. No. 5,593,792 to Farrier et al.; U.S. Pat. No. 5,595,577 to Bensalem et al.; U.S. Pat. No. 5,816,263 to Counts et al.; U.S. Pat. No. 5,819,751 to Barnes et al.; U.S. Pat. No. 6,095,153 to Beven et al.; U.S. Pat. No. 6,311,694 to Nichols et al.; and U.S. Pat. No. 6,367,481 to Nichols, et al.; US Pat. Appl. Pub. No. 2008/0092912 to Robinson et al.; and PCT WO 97/48294 and PCT WO 98/16125. See, also, those types of commercially marketed cigarettes described Chemical and Biological Studies on New Cigarette Prototypes that Heat Instead of Burn Tobacco, R. J. Reynolds Tobacco Company Monograph (1988) and Inhalation Toxicology, 12:5, p. 1-58 (2000).

Harvested biomass or one or more anatomical parts can be incorporated into smokeless tobacco products, such as loose moist snuff, loose dry snuff, chewing tobacco, pelletized tobacco pieces (e.g., having the shapes of pills, tablets, spheres, coins, beads, obloids or beans), extruded or formed tobacco strips, pieces, rods, cylinders or sticks, finely divided ground powders, finely divided or milled agglomerates of powdered pieces and components, flake-like pieces, molded processed tobacco pieces, pieces of tobacco-containing gum, rolls of tape-like films, readily water-dissolvable or water-dispersible films or strips (e.g., US Pat. App. Pub. No. 2006/0198873 to Chan et al.), or capsule-like materials possessing an outer shell (e.g., a pliable or hard outer shell that can be clear, colorless, translucent or highly colored in nature) and an inner region possessing tobacco or tobacco flavor (e.g., a Newtonian fluid or a thixotropic fluid incorporating tobacco of some form). Various types of smokeless tobacco products are set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,987,907 to Townsend; U.S. Pat. No. 5,092,352 to Sprinkle, III et al.; and U.S. Pat. No. 5,387,416 to White et al.; US Pat. App. Pub. Nos. U.S. Pat. No. 2005/0244521 to Strickland et al. and U.S. Pat. No. 2008/0196730 to Engstrom et al.; PCT WO 04/095959 to Arnarp et al.; PCT WO 05/063060 to Atchley et al.; PCT WO 05/016036 to Bjorkholm; and PCT WO 05/041699 to Quinter et al., each of which is incorporated herein by reference. See also, the types of smokeless tobacco formulations, ingredients, and processing methodologies set forth in U.S. Pat. No. 6,953,040 to Atchley et al. and U.S. Pat. No. 7,032,601 to Atchley et al.; US Pat. Appl. Pub. Nos. 2002/0162562 to Williams; 2002/0162563 to Williams; 2003/0070687 to Atchley et al.; 2004/0020503 to Williams, 2005/0178398 to Breslin et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; and 2008/0209586 to Nielsen et al., each of which is incorporated herein by reference.

An amount of harvested biomass or one or more anatomical parts added to a tobacco composition, or otherwise incorporated within a tobacco composition or tobacco product, can depend on the desired function of that harvested biomass or one or more anatomical parts, the chemical makeup of that component, and the type of tobacco composition to which the harvested biomass or one or more anatomical parts are added. When the harvested biomass or one or more anatomical parts comprise a flower or flower isolate, for example, the amount added to a tobacco composition can vary, but will typically not exceed about 5 weight percent based on the total dry weight of the tobacco composition to which the flower or flower isolate or seed or seed isolate is added. When the flower is employed within a smoking article, the amount of flower will typically be at least about 5 ppm, generally at least about 10 ppm, and often at least about 100 ppm, based on the total dry weight of the tobacco material within the smoking article; but will typically be less than about 5 percent, generally less than 2 percent, and often less than about 1 percent, based on the total dry weight of the tobacco material within the smoking article. When the flower is employed within a smokeless tobacco product, the amount of flower will typically be less at least about 5 ppm, generally at least about 10 ppm, and often at least about 100 ppm, based on the total dry weight of the tobacco material within the smokeless tobacco product; but will typically be less than about 5 percent, generally less than 2 percent, and often less than about 1 percent, based on the total dry weight of the tobacco material within the smokeless tobacco product.

Aspects of a process such as is described in various embodiments herein are further illustrated by the following examples, which are set forth to illustrate certain aspects of a process such as is described in various embodiments herein and are not to be construed as limiting thereof.

In an example, a process such as is described in various embodiments herein provides a process for inhibiting formation of nitrosamines by bacteria in tobacco, the process comprising contacting the tobacco with a substance comprising a plurality of bacteriophages capable of lysing bacteria that form nitrosamines.

In an example, a process such as is described in various embodiments herein provides a process for inhibiting chemical reduction of nitrate in a quantity of tobacco, the process comprising contacting at least a portion of the quantity of tobacco with a substance comprising a plurality of bacteriophages capable of lysing nitrate-reducing bacteria in the quantity of tobacco.

In an example, a process such as is described in various embodiments herein provides a process for decreasing the rate of formation of nitrosamines in situ in a tobacco plant, the process comprising applying and/or administering to the tobacco plant a substance comprising a plurality of bacteriophages capable of lysing nitrate-reducing bacteria in contact with the tobacco plant.

In an example, a process such as is described in various embodiments herein provides a process for decreasing the rate of formation of nitrosamines in a quantity of tobacco during post-harvest processing of the quantity of tobacco, the process comprising contacting at least a portion of the quantity of tobacco with a substance comprising a plurality of bacteriophages capable of lysing nitrate-reducing bacteria within and/or in contact with the quantity of tobacco.

In an example, a process such as is described in various embodiments herein provides a process for slowing the rate of conversion of nitrate to nitrate in a quantity of harvested and/or processed tobacco, the process comprising contacting at least a portion of the quantity of tobacco with a substance comprising a plurality of bacteriophages capable of lysing nitrate-reducing bacteria within and/or in contact with the quantity of tobacco.

In an example, a process such as is described in various embodiments herein provides a composition useful for control of nitrate-reducing bacteria in a quantity of tobacco, the composition comprising a plurality of bacteriophages capable of lysing nitrate-reducing bacteria and a suitable carrier and/or diluent.

In an example, a process such as is described in various embodiments herein provides a tobacco product possessing a diminished capacity for the formation of nitrosamines, the product comprising tobacco that has been treated with a substance comprising a plurality of bacteriophages capable of lysing nitrate-reducing bacteria in the tobacco.

In an example, a process such as is described in various embodiments herein provides a tobacco product possessing a diminished concentration of nitrosamines, the product comprising tobacco that has been treated with a substance comprising a plurality of bacteriophages capable of lysing nitrate-reducing bacteria in the tobacco.

In an example, a process such as is described in various embodiments herein provides a process wherein a plurality of bacteriophages capable of lysing a nitrate-reducing *Staphylococcus* bacterium is contacted with a quantity of tobacco in or on which a nitrate-reducing *Staphylococcus* bacterium is living for period of time sufficient for one or more of the plurality of bacteriophages to contact the *Staphylococcus* bacterium in such a manner that the one or more of the plurality of bacteriophages enter the *Staphylococcus* bacterium and cause lysis thereof.

In an example, a process such as is described in various embodiments herein provides a process wherein a plurality of bacteriophages capable of lysing a nitrate-reducing *Enterobacter* bacterium is contacted with a quantity of tobacco in or on which a nitrate-reducing *Enterobacter* bacterium is living for period of time sufficient for one or more of the plurality of bacteriophages to contact the *Enterobacter* bacterium in such a manner that the one or more of the plurality of bacteriophages enter the *Enterobacter* bacterium and cause lysis thereof.

In an example, a process such as is described in various embodiments herein provides a process wherein a plurality of bacteriophages capable of lysing a nitrate-reducing bacterium of a genus other than *Staphylococcus* or *Enterobacter* is contacted with a quantity of tobacco in or on which a nitrate-reducing bacterium of a genus other than *Staphylococcus* or *Enterobacter* is living for period of time sufficient for one or more of the plurality of bacteriophages to contact the bacterium of a genus other than *Staphylococcus* or *Enterobacter* in such a manner that the one or more of the plurality of bacteriophages enter the bacterium of a genus other than *Staphylococcus* or *Enterobacter* and cause lysis thereof.

In an example, a process such as is described in various embodiments herein provides a process wherein a contacting according to any of the above or below examples is effected in conditions of limited light or in dark conditions.

In an example, a process such as is described in various embodiments herein provides a process wherein a plurality of bacteriophages capable of lysing a nitrate-reducing bacterium listed in the *List of Prokaryotic Names Validly*

*Published* of the Leibniz-Institut DSMZ-Deutsche Sammlung von Mikroorganismen und Zellkulturen GmbH is contacted with a quantity of tobacco in or on which a nitrate-reducing bacterium listed in the *List of Prokaryotic Names Validly Published* of the Leibniz-Institut DSMZ-Deutsche Sammlung von Mikroorganismen und Zellkulturen GmbH is living for period of time sufficient for one or more of the plurality of bacteriophages to contact the nitrate-reducing bacterium listed in the *List of Prokaryotic Names Validly Published* of the Leibniz-Institut DSMZ-Deutsche Sammlung von Mikroorganismen und Zellkulturen GmbH in such a manner that the one or more of the plurality of bacteriophages enter the nitrate-reducing bacterium listed in the List of Prokaryotic Names Validly Published of the Leibniz-Institut DSMZ-Deutsche Sammlung von Mikroorganismen und Zellkulturen GmbH and cause lysis thereof.

In an example, a process such as is described in various embodiments herein provides a process wherein a plurality of bacteriophages of order or family Caudovirales, Myoviridae, Siphoviridae, Podoviridae, Microviridae, Corticoviridae, Tectiviridae, Leviviridae, Cystoviridae, Inoviridae or Plasmaviridae capable of lysing a nitrate-reducing bacterium is contacted with a quantity of tobacco in or on which a nitrate-reducing bacterium is living for period of time sufficient for one or more of the plurality of bacteriophages of order or family Caudovirales, Myoviridae, Siphoviridae, Podoviridae, Microviridae, Corticoviridae, Tectiviridae, Leviviridae, Cystoviridae, Inoviridae or Plasmaviridae to contact the bacterium in such a manner that the one or more of the plurality of bacteriophages of order or family Caudovirales, Myoviridae, Siphoviridae, Podoviridae, Microviridae, Corticoviridae, Tectiviridae, Leviviridae, Cystoviridae, Inoviridae or Plasmaviridae enter the bacterium and cause lysis thereof.

In an example, a process such as is described in various embodiments herein provides a process wherein a plurality of bacteriophages of order or family Caudovirales, Myoviridae, Siphoviridae, Podoviridae, Microviridae, Corticoviridae, Tectiviridae, Leviviridae, Cystoviridae, Inoviridae or Plasmaviridae contacted with a quantity of tobacco in or on which a nitrate-reducing bacterium is living is strictly lytic, that is, virulent.

In an example, a process such as is described in various embodiments herein provides a process wherein a plurality of bacteriophages of order or family Caudovirales, Myoviridae, Siphoviridae, Podoviridae, Microviridae, Corticoviridae, Tectiviridae, Leviviridae, Cystoviridae, Inoviridae or Plasmaviridae contacted with a quantity of tobacco in or on which a nitrate-reducing bacterium is living does not engage in transduction of non-viral DNA.

In an example, a process such as is described in various embodiments herein provides a process wherein a plurality of bacteriophages of order or family Caudovirales, Myoviridae, Siphoviridae, Podoviridae, Microviridae, Corticoviridae, Tectiviridae, Leviviridae, Cystoviridae, Inoviridae or Plasmaviridae contacted with a quantity of tobacco in or on which a nitrate-reducing bacterium is living possesses a broad host range within the target species and/or genus.

In an example, a process such as is described in various embodiments herein provides a process wherein a plurality of bacteriophages of order or family Caudovirales, Myoviridae, Siphoviridae, Podoviridae, Microviridae, Corticoviridae, Tectiviridae, Leviviridae, Cystoviridae, Inoviridae or Plasmaviridae contacted with a quantity of tobacco in or on which a nitrate-reducing bacterium is living has been propagated on a non-pathogenic host.

In an example, provided herein is a process for inhibiting formation of nitrosamines by bacteria in and/or on tobacco, the process comprising contacting the tobacco with a substance comprising a plurality of bacteriophages capable of lysing bacteria that form nitrosamines.

In an example, provided herein is a process for inhibiting chemical reduction of nitrate in and/or on a quantity of tobacco, the process comprising contacting at least a portion of the quantity of tobacco with a substance comprising a plurality of bacteriophages capable of lysing nitrate-reducing bacteria in the quantity of tobacco.

In an example, provided herein is a process for decreasing the rate of formation of nitrosamines in situ in and/or on a tobacco plant, the process comprising applying and/or administering to the tobacco plant a substance comprising a plurality of bacteriophages capable of lysing nitrate-reducing bacteria in contact with the tobacco plant.

In an example, provided herein is a process for decreasing the rate of formation of nitrosamines in and/or on a quantity of tobacco during post-harvest processing of the quantity of tobacco, the process comprising contacting at least a portion of the quantity of tobacco with a substance comprising a plurality of bacteriophages capable of lysing nitrate-reducing bacteria within and/or in contact with the quantity of tobacco.

In an example, provided herein is a process for slowing the rate of conversion of nitrate to nitrate in and/or on a quantity of harvested and/or processed tobacco, the process comprising contacting at least a portion of the quantity of tobacco with a substance comprising a plurality of bacteriophages capable of lysing nitrate-reducing bacteria within and/or in contact with the quantity of tobacco.

In an example, provided herein is a composition useful for control of nitrate-reducing bacteria in a quantity of tobacco, the composition comprising a plurality of bacteriophages capable of lysing nitrate-reducing bacteria and a suitable carrier and/or diluent.

In an example, provided herein is a tobacco product possessing a diminished capacity for the formation of nitrosamines, the product comprising tobacco that has been treated with a substance comprising a plurality of bacteriophages capable of lysing nitrate-reducing bacteria in the tobacco.

In an example, provided herein is a tobacco product possessing a diminished concentration of nitrosamines, the product comprising tobacco that has been treated with a substance comprising a plurality of bacteriophages capable of lysing nitrate-reducing bacteria in the tobacco.

Many modifications and other embodiments of a process such as is described in various embodiments herein will come to mind to one skilled in the art to which this disclosed process pertains having the benefit of the teachings presented in the foregoing description. Therefore, it is to be understood that a process such as is described in various embodiments herein is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A process for inhibiting formation of nitrosamines by bacteria in and/or on planted tobacco, the process comprising treating the planted tobacco with a substance comprising a plurality of bacteriophages capable of lysing nitrate-reducing bacteria that form nitrosamines, wherein the substance comprising the plurality of bacteriophages includes one or more bacteriophages from order or family Caudovirales, Myoviridae, Siphoviridae, Podoviridae, Microviridae, Corticoviridae, Tectiviridae, Leviviridae, Cystoviridae, Inoviridae or Plasmaviridae, wherein the treating comprises administering to the tobacco plant the substance comprising the plurality of bacteriophages, wherein the nitrate-reducing bacteria are free from transduction of non-viral DNA; and slowing the rate of conversion of nitrate to nitrite on the planted tobacco by lysing at least a portion of the nitrate-reducing bacteria.

2. The process of claim 1, wherein the administering comprises spraying.

3. The process of claim 1, wherein the administering comprises contacting a mixture comprising the substance comprising the plurality of bacteriophages with one or more anatomical parts of the tobacco plant.

4. The process of claim 3, wherein the one or more anatomical parts comprise a leaf or a portion thereof.

5. The process of claim 3, wherein the one or more anatomical parts comprise a root or a portion thereof.

6. The process of claim 1 further comprising a step of administering the substance comprising the plurality of bacteriophages in and/or on a quantity of tobacco during post-harvest processing of the quantity of tobacco.

7. The process of claim 6, wherein the quantity of tobacco comprises harvested tobacco leaf.

8. A tobacco product possessing a diminished capacity for the formation of nitrosamines and/or a diminished concentration of nitrosamines, the product comprising tobacco with a diminished capacity of for formation of nitrosamines, wherein the tobacco with the diminished capacity of for formation of nitrosamines was in contact with nitrate-reducing bacteria free from transduction of non-viral DNA prior to harvest, wherein the tobacco was treated with a substance comprising a plurality of bacteriophages capable of lysing the nitrate-reducing bacteria in contact with the tobacco before the tobacco was harvested, wherein the substance comprising the plurality of bacteriophages includes one or more bacteriophages from order or family Caudovirales, Myoviridae, Siphoviridae, Podoviridae, Microviridae, Corticoviridae, Tectiviridae, Leviviridae, Cystoviridae, Inoviridae or Plasmaviridae and wherein the treatment with the substance comprising the plurality of bacteriophage slowed the rate of conversion of nitrate to nitrite on the tobacco by lysing at least a portion of the nitrate-reducing bacteria.

9. The product of claim 8, wherein the product is a smokeless tobacco product.

10. The product of claim 8, wherein the product is a smokable tobacco product.

11. The product of claim 8, wherein the product is a smokeless tobacco product.

12. The product of claim 8, wherein the product is a smokable tobacco product.

13. A method of providing a tobacco product with a diminished capacity for formation of nitrosamines, the method comprising:

treating a planted tobacco in contact with nitrate-reducing bacteria free from transduction of non-viral DNA with a substance comprising a plurality of bacteriophages capable of lysing bacteria that form nitrosamines and a carrier, wherein the substance comprising the plurality of bacteriophages includes one or more bacteriophages from order or family Caudovirales, Myoviridae, Siphoviridae, Podoviridae, Microviridae, Corticoviridae, Tectiviridae, Leviviridae, Cystoviridae, Inoviridae or Plasmaviridae, wherein the contacting comprises administering to the tobacco plant the substance comprising the plurality of bacteriophages via spraying on at least a portion of the planted tobacco's roots and leaves;

slowing the rate of conversion of nitrate to nitrite on the planted tobacco by the plurality of bacteriophage lysing at least a portion of the nitrate-reducing bacteria in contact with the planted tobacco;

harvesting the treated planted tobacco, wherein the harvested tobacco has a diminished capacity of for formation of nitrosamines;

processing the harvested tobacco plant by administering the substance comprising the plurality of bacteriophages to the harvested tobacco, wherein processed harvested tobacco has a further diminished capacity of for formation of nitrosamines.

\* \* \* \* \*